United States Patent [19]

Rothman et al.

[11] Patent Number: 4,837,162
[45] Date of Patent: Jun. 6, 1989

[54] NON-FLUORESCING, NON-REFLECTIVE POLYAMIDE FOR USE IN DIAGNOSTIC TESTING

[75] Inventors: Isaac Rothman, Brooklyn; Peter J. Degen, Huntington, both of N.Y.

[73] Assignee: Pall Corporation, New York, N.Y.

[21] Appl. No.: 58,843

[22] Filed: Jun. 5, 1987

[51] Int. Cl.⁴ .................. G01N 33/545; G01N 33/546
[52] U.S. Cl. ..................................... 436/531; 435/180;
436/165; 436/172; 436/532; 436/533; 436/534
[58] Field of Search ............... 436/531, 532, 533, 165,
436/172, 534; 435/180

[56] References Cited

U.S. PATENT DOCUMENTS

| | | | |
|---|---|---|---|
| 3,970,597 | 7/1976 | Sokolovsky | 435/180 X |
| 4,584,277 | 4/1986 | Ullman | 436/531 X |
| 4,588,697 | 5/1986 | Khanna | 436/531 X |
| 4,615,985 | 10/1986 | Deutsch | 436/531 |
| 4,680,275 | 7/1987 | Wagner | 436/531 X |
| 4,693,985 | 9/1987 | Degen | 436/531 |

OTHER PUBLICATIONS

Jolley, M. E. et al., J. Immunol. Methods, 67(1), 21–35.

Primary Examiner—Sidney Marantz
Attorney, Agent, or Firm—Leydig, Voit & Mayer

[57] ABSTRACT

A polyamide dyed with a reactive dye capable of absorbing incident light of the excitation waveband of a fluorophore or light of the emission waveband of the polyamide is provided for use in assays in which the presence or quantity of an analyte is being detected by fluorescence as a result of excitation of a fluorescent material at an excitation waveband of light and in which the excitation waveband impinges upon the polyamide.

10 Claims, 1 Drawing Sheet

NON-FLUORESCING, NON-REFLECTIVE POLYAMIDE FOR USE IN DIAGNOSTIC TESTING

BACKGROUND OF THE INVENTION

1. Technical Field

The present invention relates to solid support materials used in diagnostic assays involving binding reactions, particularly antibody binding reactions, in which a fluorescent signal is used to detect the presence of bound analytes.

2. Background

There has been a rapid increase in the number and types of analyses employed to detect the presence or amount of analytes in samples of various origins in recent years. Most of these assays utilize the binding of one chemical or biological entity by another as the primary event by which an analyte is detected. However, this primary recognition event is not itself detectable by the person carrying out the assay since this binding interaction takes place on a submicroscopic level. Such assays therefore require the use of some detectable signal by which binding interactions themselves can be detected.

A number of detection techniques involve fluorescence. Solid-phase fluorescence immunoassays have been described in publications since 1965. However, techniques relying on fluorescence for detection of the binding interaction suffer from limitations that prevent them from achieving their theoretical limit of sensitivity. Two factors significantly affecting sensitivity are background fluorescence and light scattering by solid materials in contact with the reaction media, such as substrates to which reactants are attached or walls of containers in which measurements are made. These phenomena arise from the use of a light beam to excite the fluorescent signal material (fluorophore) being detected. The light used for excitation is of a shorter wavelength than the waveband of light emitted by the fluorescent material and accordingly does not normally interfere with the signal measurement itself. However, light in the excitation waveband may also cause fluorescence of the support material, thereby interfering with the sensitivity of detection when the emission waveband of the solid support overlaps the emission waveband of the fluorophore. Additionally, light scattering from ambient light of the wavelength being detected also interferes with detection of primary fluorescence by the signal material in some cases.

These problems are particularly acute when the solid is a polyamide. A number of studies show that light-stimulated endogenous fluorescent emissions and light reflection, from nylon-6,6 in particular, can coincide with the range of UV-visible wavelengths emitted from fluorophore-tagged analytes. Other materials utilized as solid supports also fluoresce and reflect light, but these materials do so to a lesser extent than polyamides. At the same time, recent developments in polyamide chemistry have created microporous membranes and other nylon materials having properties that are extremely useful in binding assays, such as controlled porosity, wettability, and enhanced surface charge.

Accordingly, there is a need for polyamide materials that will not exhibit background fluorescence or light reflectance to a degree that interferes with reliable detection of fluorescent emissions from fluorophore-tagged analytes. These materials also must retain the chemical and physical properties that give them their advantageous properties for use in analytical assays of the type described.

3. Relevant Literature

A number of review articles on fluorescence immunoassays have been published. See, for example, Jolley et al., *Journal of Immunological Methods* (1984) 67:21-35, and references cited therein. A study of a number of polymer substances for light absorbing and emission properties using UV-visible derivative spectroscopy is set forth in Allen, *Polymer Photochemistry* (1981) 1:43-55. A number of different dyes useful in carrying out the present invention are described in Lienhard et al., U.S. Pat. No. 4,527,994.

SUMMARY OF THE INVENTION

In order to overcome the numerous difficulties in the prior art, particularly involving fluorescence and scattering of light by polyamide solid materials, the present invention provides optically passive polyamides for use in diagnostic assays in which the presence or quantity of an analyte is being detected by fluorescence. The optically passive polyamides are prepared by dyeing a polyamide substrate with a dye capable of absorbing some or all light from the excitation waveband of a fluorescent signal material or polyamide substrate or some or all light from the emission waveband of the fluorescent signal material or polyamide substrate or a combination thereof. By using an acid reactive dye capable of integrally binding to the polyamide, the properties of the nylon substrate are not adversely affected. For example, prior to the present invention it was not possible to use a microporous polyamide membrane filter of the type described in U.S. Pat. No. 4,340,479 in a fluorescent assay because of excessive background fluorescence. The present invention provides optically passive microporous polyamide membrane filters of this type while retaining the desirable porosity and surface characteristics.

Any polyamide material can be modified in the fashion described to produce a material having reduced background fluorescence and light scattering properties. For example, the polyamide can form or be part of the walls of a container, beads or other particles suspended in solution, or a porous membrane used to collect suspended material. The invention is particularly useful for preparing hydrophilic, porous polyamide membrane filters for use in fluorimetric assays.

BRIEF DESCRIPTION OF THE DRAWINGS

The present invention will be better understood by reference to the following detailed description of specific embodiments when considered in connection with the drawings that form part of this specification, wherein.

DESCRIPTION OF SPECIFIC EMBODIMENTS

Figure 1:
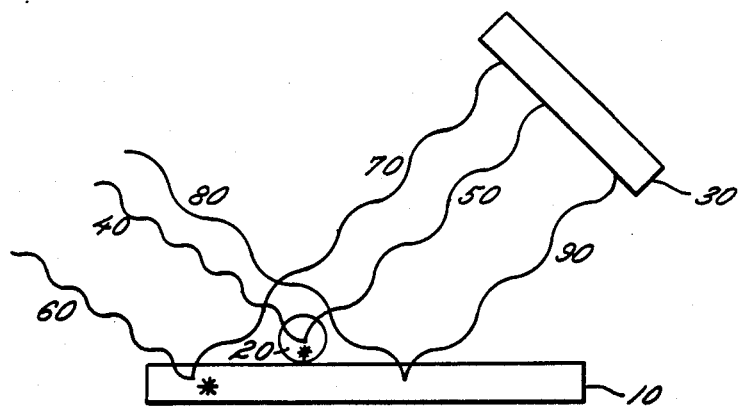
FIG. 1 is a schematic diagram showing detection of a fluorescent signal and interfering light emitted or reflected from a polyamide surface.

The present invention is directed to polyamide materials for use in assays in which the presence of an analyte is detected by a binding interaction and in which the detectable signal is a fluorescent event. The invention allows polyamides to be used as solid supports or reaction containers by providing a polyamide substrate dyed with a reactive dye capable of absorbing some or all of light of the excitation waveband of a fluorescent material being used to generate a fluorescent signal in the assay. Alternatively, the dyed polyamide is capable of absorbing some or all of incident light from the emission waveband. By using a reactive dye, dyed polyamides can be obtained without adversely affecting the surface characteristics of the polyamide. By selecting the dye according to its absorbance spectrum, the dyed polyamides of the invention provide increased sensitivity in fluorescence assays.

The invention can be practiced with any type of polyamide substrate, whether used as a solid support or as a reaction container. The invention provides an improved polyamide material that can be used as any container surface, filtering membrane, reaction substrate, or the like. The invention is particularly useful in providing microporous polyamide materials used as membrane filters. These polyamide materials contain large numbers of microscopic pores that must remain unchanged by dyeing if the membrane is to function properly. Careful selection of a dye that produces the desired absorbance of light while retaining the physical characteristics of the solid polyamide is therefore required.

The preparation and use of polyamides as solid supports or containers in binding assays do not themselves constitute a part of the present invention since the preparation and use of such materials are well known. Nevertheless, a brief description of the polyamides themselves is provided for completeness.

Polyamide materials are organic polymers formed by the formation of amide bonds between monomers of one or more types. When a single monomer is used, the monomer contains both an amino group and carboxylic acid group. These monomers joined together in a head-to-tail fashion when the carboxylic acid group at one end of a monomer reacts with the amino group at the other end of a secod monomer. Polyamides are also formed from two monomers one of which contains two acid groups and the other two amino groups. The resulting polymer is a linear chain of alternating acid- and amino-containing monomers. The class of polyamides known as nylons comprises aliphatic carbon chains, usually alkylene groups, between amide groups. Nylon 6,6 is such a linear chain formed from adipic acid and hexamethylenediamine monomers. Numerous other polyamides can be formed using other monomers and mixtures thereof.

Polyamides can be prepared into solid supports, containers, and filters by various manufacturing processes, many of which have been specifically developed for nylons. Preferred nylon substrates will be formed from a liquophilic, microporous membrane or other porous material, typically having an absolute pore rating of about 0.001 to about 20 microns, preferably about 0.02 to about 8 microns, and most preferably about 0.2 to about 3 microns. The substrate preferably is also skinless. Materials which are suitable for use as membrane filters also have void volumes in the range of about 60–90%, preferably in the range of about 75–90%. Nylon 6,6 is a preferred polyamide, particularly in the form of a skinless, hydrophilic microporous membrane filter as described in U.S. Pat. No. 4,340,479. By skinless is meant that the character of the polymer organization (e.g., crystalline vs. amorphous regions) does not change from the exterior surface to the interior of the polyamide. This is in contrast to, for example, extruded fibers which have a dense crystalline outer "skin", resulting from the extrusion process, with a more amorphous central portion.

Liquophilicity, as used herein, refers to the wettability of the membrane by the liquid(s) with which it is contacted. The wettability or liquophilicity of a solid structure, e.g., a membrane, is a function of that structure's surface energy and the surface tension of the applied liquid. If the surface energy is at least as high as the surface tension of the liquid, the liquid will spontaneously wet the solid structure. For example, a microporous membrane having a surface energy of 72 dynes/cm or higher will be wetted by aqueous solutions that have a surface tension of at least 72 dynes/cm; i.e., it is hydrophilic.

The capability of a solid structure (membrane or otherwise) to be wetted by a liquid can be determined by placing a drop of liquid on the porous structure. The angle of contact provides a quantitative measure of wetting. A very high angle of contact indicates poor wetting, while a zero angle of contact defines complete or perfect wetting. Materials used in the subject invention as a wettable or liquophilic porous substrate are characterized by being readily or spontaneously wetted by the applied liquid and have a low angle of contact with the applied liquid. Indeed, when a drop of a test liquid(s) is placed on a spontaneously wettable or liquophilic microporous substrate, the drop of liquid penetrates and wets the substrate, effectively providing a zero angle of contact therewith.

Wettability may also be expressed in terms of intrusion pressure which is defined as the applied pressure required for liquid to penetrate into the pores of the substrate. Materials which are particularly preferred for the substrate have intrusion pressures of or close to zero when water is the liquid.

Some of the materials which are suitable or preferred for use as in the present invention are intrinsically hydrophilic or water-wettable. For example, BIODYNE$^R$ is an N66 polyamide, microporous membrane commercially available from Pall Corporation which is inherently water-wettable by virtue of its method of manufacture (see U.S. Pat. No. 4,340,479). Other polyamides can be chemically modified to render them hydrophilic. Some preferred polyamides contain chemically modified polymer strands containing modifying monomers that change the physical properties of the nylon.

Nylon materials may also be capable of being treated with and retaining or immobilizing a substance being analyzed and/or a reactant which may be used to perform a specified test or reaction with the substance being analyzed for in a sample. The reactant, which may be of ionic, molecular, or macromolecular nature, may be immobilized on the polyamide surface by strong physical forces or by being bonded in some manner, such as covalant chemical coupling, to the surface. As employed herein, the term "surface" or "surface area" refers not only to the gross surface(s) of the structure but also, in those cases where a microporous structure such as a membrane is under consideration, to the surfaces of the micropores, i.e., the interior surfaces of the structure which are contacted by fluid during use.

Materials which are preferred for use as a solid support have large surface areas. This feature permits a greater amount or higher concentration of reactant to be immobilized in the substrate. accordingly, higher sensitivities may be achieved.

Polyamides preferred for use in the present invention include nylons of the type described in U.S. Pat. No. 4,340,479 (described above), which is incorporated herein by reference. Other microporous membrane materials include AMINODYNE TM, HYDROXYDYNE TM, POSIDYNE TM, ULTIPOR N66 TM, and IMMUNODYNE TM, all available from Pall Corporation. IMMUNODYNE TM is a modified CARBOXYDYNE$^R$ membrane, which is also available from Pall Corporation. CARBOXYDYNE$^R$ is a hydrophilic, microporous, skinless nylon 6,6 membrane with controlled surface properties formed by the cocasting process described in U.S Patent Application Ser. No. 850,061, as discussed below, specifically by cocasting nylon 6,6 and a polymer containing an abundance of carboxyl groups to form a membrane having controlled surface properties characterized by carboxyl functional groups at its surfaces. IMMUNODYNE$^{TM}$ membranes may be prepared from CARBOXYDYNE$^R$ membranes by treating them with trichloro-s-triazine in the manner described in U.S. Patent Application Ser. No. 642,899, discussed below.

Also included among the preferred polyamide membranes for the present invention are hydrophilic, microporous, skinless polyamide membranes with controlled surface properties of the type described in (1) U.S. Patent Application Ser. No. 850,061, filed Apr. 7, 1986, Pat. No. 4,707,266, which is a Continuation Application of U.S. Patent Application Ser. No. 459,956, filed Jan. 21, 1983, Pat. No. 4,599,956, which in turn is a Continuation-In-Part Application of U.S. Patent Application Ser. No. 346,118, filed Feb. 5, 1982, now abandoned, and in (2) U.S. Patent Application Ser. No. 848,911, filed Apr. 7, 1986, Pat. No. 4,702,840, which is a Continuation Application of U.S. Patent Application Ser. No. 460,019, filed Jan. 2, 1983, now abandoned, which is a Continuation-In-Part Application of U.S. Patent Application Ser. No. 346,119, filed Feb. 5, 1982, now abandoned. All of the aforementioned U.S. patent applications are specifically incorporated herein by reference.

The monomers and polymers used to modify the polyamide membranes with controlled surface properties comprise polymers which contain substantial proportions of chemical functional groups, such as hydroxyl, carboxyl, amine, and imine groups. As a result, the membranes include, at their surfaces and throughout their interior spaces, high concentrations of functional groups such as hydroxyl, carboxyl, imine, or a combination of any of the above groups which do not react with one another. These polyamide membranes having controlled led surface properties have higher concentrations of carboxyl or imine groups at their surfaces than the polyamide membranes which do not have controlled surface properties, i.e., those which are formed from the polyamide resin but are not cocast with the modifying polymer.

The invention also applies to polyamide materials used in close connection with fluorescent assays but in which there is no specific interaction between one of the reactants and a solid surface. For example, it is possible to carry out fluorescent assays in containers which are made in whole or in part from polyamides. Fluorescence by the container walls under the influence of light from the excitation waveband can interfere with measurement of fluorescence under these circumstances. Accordingly, the present invention also applies to container walls, such as the walls of microtiter plates, utilized in carrying out fluorescent assays and to other polyamide materials in the vicinity of the reaction medium when fluorescence is being measured.

A preferred aspect of the invention is achieved when a polyamide membrane of the invention is prepared for use in a particle concentration fluorescence immunoassay (PCFIA) of the type described in Jolley et al., Journal of Immunological Methods, (1984) 67:21–35, which is herein incorporated by reference. In such assays, one member of a binding pair, for example an antigen, is bound to submicron polystyrene or other polymeric particles. The other member of the binding pair is the analyte being detected. In the example under consideration, this analyte would be the antibody that reacts specifically with the antigen bound to the particle surface. A fluorescein-labeled second antibody or the other labeled antibody is used to generate the detectable signal. The reaction is carried out in a multi-well plate having a filter, in this case a polyamide membrane filter, that forms the bottom surface of the wells. After reaction has taken place between the suspended particles in the multi-well plate wells and the sample solutions in the wells, the solid phase is separated from the reaction mixture by filtration, which traps the particles on the membrane at the bottom of the wells. Fluorescence readings are generally taken by front-surface fluorometry. This technique involves irradiating the particles, which are in contact with membrane, and reading fluorescence from the emission waveband, this reading being taken from the illuminated surface. The present invention eliminates background fluorescence from the polyamide membrane when the top surface of this membrane is being illuminated by the excitation waveband. Accordingly, higher sensitivity is achieved by a reduction in background fluorescence.

The other key component in preparing a non-fluorescing solid polyamide of the invention is a dye capable of providing the required absorbance waveband without interfering with the desirable properties, such as porosity, hydrophilicity, and other surface properties of the polyamide membranes. Mixtures of dyes can be used in addition to individual dyes. Numerous dyes have been tested which are not appropriate. Many dyes are not capable of dyeing the polyamide surface while others adversely affect the surface properties.

The dyes used in the practice of the present invention are dyes reactive with nylon. Reactive dyes form a well-known class of dye stuffs in which the dye contains a functional group that reacts chemically with the material being dyed. In particular, acid reactive dyes typically contain sulfate, sulfonic acid, carboxylic acid, or other acid groups that form chemical bonds with basic groups present in the solid being dyed (e.g., terminal amino groups in polyamide strands). Acid reactive dyes of the azo class are particularly useful in the practice of the present invention since such dyes can be readily manipulated to absorb light in the necessary waveband. Azo dyes have the general formula Ar—N=N—Ar', in which Ar and Ar' represent aromatic ring systems.

These ring systems can be hydrocarbyl rings, such as benzene or napthalene, or can be heterocyclic rings, such a pyrrole, pyrazole, oxazole, quinoline, pyrimidine, purine, isoquinoline, carbazole, and the like. Functional groups present on the aromatic rings include halogen, $C_1$–$C_4$ alkykl, amino, amino substituted with one or two $C_1$–$C_4$ alkyl groups, $C_1$–$C_4$ alkylsulfonyl, sulfonylmide, nitro, and other aromatic rings, which are typically attached directly to the first aromatic ring or bridged thereto by an alkylene group in order to provide conjugation between the two rings. Of course, an acid-reactive group must also be present if the dye is to be an acid-reactive dye. Preparation of such azo dyes and selection of various aromatic rings and substitution patterns to provide for the desired absorption of light are described in numerous texts and review articles, such as Zollinger, *Azo and Diazo Chemistry*, Interscience, New York, 1961, which is herein incorporated by reference. Selection of a dye or group of dyes for particular application according to its absorbance spectrum is described later in this specification.

Preferred acid reactive dyes are non-metalic. For example, Nylanthrene ™, an acid dye manufactured by Crompton and Knowles, is a preferred dye of the invention and does not contain any metal. Premetalized sulfonic acid azo dyes, such as Irgalan BGL200 ™ from Ciba-Geigy, are capable of providing a dyed polyamide of the invention, although the surface so prepared may be limited in its biological applications because of the presence of metal which interfers with some proteinacious binding reactions. Nonetheless, such surfaces are useful for some analytes and binding reactions and are therefore within the scope of the present invention. For example, 1:2 chromium complexes of a pyrazolone dye and a $\beta$-naphtholazo dye are described in detail in U.S. Pat. No. 4,527,994, which is herein incorporated by reference.

Some acid reacting dye mixtures advertised by their manufacturers as being capable of dyeing nylon fibers black are not effective in dyeing skinless microporous membranes black. However, such dyes can still be used for individual fluorophores if absorbance spectra of the dyes are matched to emission and excitation wavebands, as described in this specification.

The polyamide surfaces of the invention are generally dyed by preparing an aqueous solution or dispersion of the dye, which may be stablilized with a dispersant. To increase the rate of dyeing, additives such as salts (e.g., ammonium acetate, sodium acetate, or monosodium phosphate) or acids (e.g., formic acid) can be added to the dye bath. Other components, such as leveling agents to provide evenly dyed surfaces, can also be included in the dye bath. Alkanylethoxy condensates (e.g., Cenegen NWA ™ from Crompton-Knowles) is a suitable leveling agent for non-metalic azo acid reactive dyes. Ammonium sulfate can also be used as a leveling agent. Solutions (rather than suspensions) of dyes are strongly preferred in order to prevent suspended dye particles (as opposed to molecules) from adhering to and adversely affecting the surface of the polyamide, particularly porous polyamides.

Typically, a dye bath containing an immersed membrane to be dyed is heated in a controlled manner from about 40°–50° C. to about 80°–95° C. The polyamide is maintained in the heated, agitated bath for a sufficient time, typically about 30 minutes, to allow dyeing of its surfaces. The temperature is typically reduced to about 40°–50° C. before removing the dyed article from the bath. The dyed solid is washed with deionized water to remove unreacted dye prior to drying. Variations in this technique required by variations in the structure of the dyes and polyamides will be readily apparent to those of skill in the art of dyeing polyamides. The suitability of any dyeing procedure can readily be determined by measuring the fluorescence or lack thereof of the dyed polyamide.

Dyes can be selected for particular applications by choosing a dye having an absorption waveband that overlaps, either fully or partially, either the waveband of light that is to be used in including fluorescence of a particular fluorescent signal or the waveband of light that would be emmitted by the fluorescent signal when excited by light of the excitation waveband. Particularly preferred are dyed nylons that have a black appearance when viewed in either visible or ultraviolet light. By providing an entirely black surface, the solid nylon used in the diagnostic assay will provide a high color contrast background which will further improve detection, resolution, and measurement of fluorescent emissions from fluorophore-tagged analytes as well as providing a background for comparison of color from test-related color bodies adjacent to the dyed surfaces. However, it will be realized that even partial reduction in the background fluorescence will be advantageous in achieving increased sensitivity. For example, if the background fluorescence is reduced to one-half or one-tenth of the normal level for the undyed polyamide, sensitivity can be increased by two-fold or ten-fold, respectively, assuming that all other characteristics of the system are unchanged. Thus, even a 10% reduction in background fluorescence and/or reflection of incident light can be useful, although it is preferred to reduce background fluorescence and/or reflection by 50%, more preferably by 75%, and even more preferably by at least 90%. The most preferred embodiments of the invention are those in which background fluorescence and reflectance is reduced to essentially zero.

The waveband of light which must be absorbed by dyes in order to achieve the desired results of the present invention depend on whether the dyed nylon is intended for use in a variety of different assays or is designed for use in a single assay with a single excitation waveband. If a nylon surface is to be used in a wide variety of assays using different excitation wavebands, the dye should absorb over a wide range of wavelenghts. If the surface is to be used in a single test, a dye having a narrow absorbance spectrum can be used. Of course, the useful absorbance spectrum for a dye depends to some extent on the apparatus in which the dyed surface is to be used. Many fluorescent measurements are carried out in a closed container by using a filter or prism to select a narrow waveband of ultraviolet light with which to excite the fluorescent molecules being detected. In such instruments, it is only necessary that the dye absorb in this narrow excitation waveband, particularly if ambient light is excluded from the chamber in which measurement is taking place. Thus, there is no requirement for matching the waveband of the dye with the emission waveband of the nylon material. On the other hand, if ambient light is present or if a broad excitation waveband is used, it becomes more important to match the absorbance spectrum of the dye with the entire excitation waveband of the polyamide material. The same is true if the solid polyamide is to be used in a variety of assays in which different wavebands of ultraviolet light will be used to excite different detectable fluorescent molecules.

As an alternative to selecting absorbance spectra for dyes that match the excitation wavebands, an absorbance spectrum can be selected that overlaps the emission waveband of the polyamide. Thus, even if ultraviolet light within the excitation waveband of the polyamide strikes the surface, the emitted light will be absorbed.

The process of matching dye absorbances to emission and excitation wavebands is shown in the attached figures. FIG. 1 shows an undyed polyamide membrane 10 having a particle 20 on its surface. The signal-generating fluorophore resides on the surface of particle 20. A detector 30 is provided to read the signal. When incident light 40 of proper wavelength strikes the fluorophore on particle 20, fluorescence occurs as indicated by a star (*). Light of a longer wavelength 50 is emitted and is detected by detector 30.

Background fluorescence is caused by light 60 striking polyamide surface 10. If this light is within the excitation waveband of the polyamide, fluorescence occurs as indicated by the star. Emitted light 70 can then be detected as background fluorescence by detector 30. Detector 30 can also detect incident ambient light 80 which is reflected from polyamide surface 10 as indicated by light path 90. If the reflected light 90 is within the detection waveband, the background reading will be increased. As indicated in FIG. 1, detector 30 cannot distinguish a signal 50 from background fluorescence 70 or reflected light 90, so that sensitivity of the assay is compromised.

Figure 2:
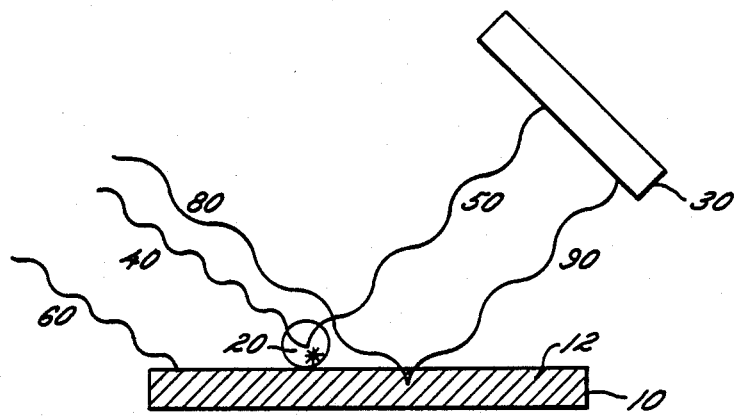
FIG. 2 is a schematic diagram showing reduction in background fluorescence when a polyamide substrate is dyed with a dye capable of absorbing light from the excitation waveband.

FIG. 2 shows an otherwise similar situation in which substrate 10 has been dyed to provide an optically passive polyamide 12 capable of absorbing incident light 60 having the same wavelength as the light 40 used to excite the fluorescence signal on particle 20. Since the dye prevents light from reaching or reduces the intensity of light reaching undyed polyamide, little or no fluorescence occurs. Thus, background fluorescence is reduced (i.e., background fluorescence 70 of FIG. 1 is missing). Choosing a dye having an absorbance spectrum that matches only excitation wavelength 40 does not prevent incident ambient light 80 from being reflected (90) and detected. However, many fluorescence measurements, as indicated above, are made in closed containers to block out ambient light.

It should be noted that the wavelength of light 60 is presumed to be the same as that of light 40 because the light measurement is taking place in a fluorometer which presents a narrow waveband of excitation light. If a broad excitation waveband is provided, dyed polyamide 12 should be selected to absorb light in the excitation waveband of the polyamide (rather than just the excitation waveband of the fluorophore) if any light in the excitation waveband would produce a fluorescent event in the polyamide that would produce emitted light of the wavelength being detected by detector 30.

Figure 3:
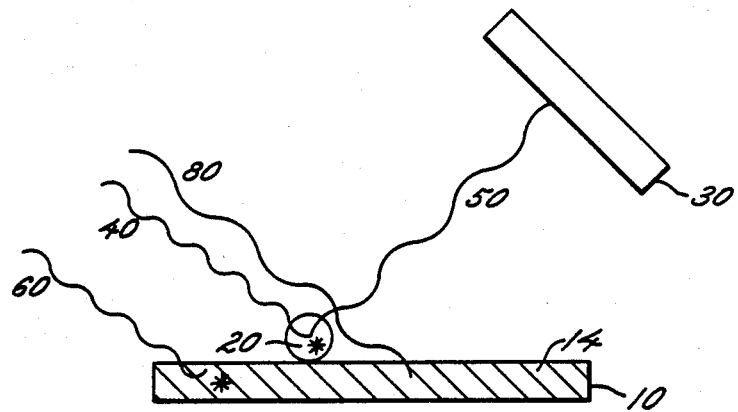
FIG. 3 is a schematic diagram showing reduction in background fluorescence and reflected light when a polyamide substrate is dyed with a dye capable of absorbing light in the emission waveband being detected.

FIG. 3 shows a similar diagram in which substrate polyamide 10 is dyed (14) using a dye selected to have an absorbance spectrum matching the emission spectrum of the fluorophore present on particle 20. In this case, although incident light 60 reaches a polyamide 10 and a fluorescent event takes place as indicated by the star, dye 14 blocks the emitted light, thereby eliminating background fluorescence. Similarly, incident ambient light 80 having a wavelength equal to that of emitted light 50 from the fluorophore is absorbed by the dye and not reflected. Accordingly, a dye having an absorbance spectrum which overlaps the emission spectrum of the fluorophore blocks both background fluorescence and reflected light in the interferring wavelength range.

Although not illustrated in a figure, it is also possible to produce a dyed surface using a dye or mixture of dyes tht provide an absorbance spectrum covering both the excitation and emission wavebands. Such a dyed surface would work by both mechanisms described above.

The phrase excitation waveband is used in this specification to describe the range of wavelengths of light at which a fluorescent material absorbs light. This waveband is sometimes referred to in the scientific literature as an absorption spectrum or absorption waveband, but these terms are not used to describe properties of fluorescent materials in the present specification in order to prevent confusion with the absorption spectrum of the dye. When fluorescence is being measured in a device that provides a waveband of excitation light narrower than the total excitation waveband, "excitation waveband" can refer to the waveband provided by the device, as will be clear from the context of the phase. The emission waveband is the range of wavelengths of light at which light is emitted (or detected; see discussion above regarding excitation) during fluorescence.

Signal-producing fluorescent materials utilized in immunoassays and other analytical assays involving binding are often referred to as fluorophores. The word fluorophore refers to the molecule or part thereof that fluoresces. The main types of fluorophores currently used as labels in such assays are fluorescein, rhodamine, umbelliferone, and lanthanide chelates and the derivatives of these components. Fluorescein is the most commonly used fluorophore, in part because of its availability in an activated form for direct coupling to the antibody or antigen utilized in a binding assay. Fluoroscein isothiocyanate is the most commonly used reagent.

The excitation wavebands of commonly used fluorophores typically fall in the range of from about 250 to 550 nm. The wavelengths of maximum absorption in the excitation waveband is 492 nm for fluoroscein, 550 nm for rhodamine, 380 nm for umbelliferone, and about 330 nm for lanthonide chelates. Emission wavebands are typically narrower than excitation wavebands and are shifted to longer wavelengths (a Stokes shift). Typical bandwidths are on the order of 50–150, generally about 100 nm. Wavelengths of maximum emission are 518 nm for fluoroscein, 585 nm for rhodamine, 450 nm for umbelliferone, and about 613 nm for a typical lanthonide chelate.

Accordingly, dyes that absorb in the indicated excitation wavebands are those which find most use in the practice of the present invention, since such dyes absorb the typically narrow waveband of light from the fluorometer (that is used to excite the fluorophore) before the polyamide can absorb the light and fluoresce. Likewise, since fluorometers also typically measure light from emissions in a narrow waveband, dyes that absorb in the indicated emission wavebands will also be commonly used in the practice of the present invention, since such dyes will absorb the light emitted from the polyamide before it can escape from the surface of the polyamide material. Accordingly, dyes have absorbance spectra centered on the wavelengths of maximum absorption and maximum emission for fluorophores, such as are described in the previous paragraph, are preferred. Dye absorbance wavebands preferably have band widths of at least 50 nm, more preferably at least 100 nm. Dyes and dye mixtures having high levels of absorbance throughout the ultraviolet and visible waveband (from about 250 to about 770 nm with about 400 nm being the border between ultraviolet and visible light) are particularly preferred. Different efficiencies in absorbing light can be taken into consideration by including greater or lesser amounts of the dye in the polyamide material. Dyes having higher molar absorbances are preferred over dyes having lesser absorbances. Thus, the polyamide membrane surface can be made completely absorbing without interfering with the emission of light from the fluorophores on tagged analytes on particles residing on the membrane surface.

A review of fluorescent-labeled immunoassays, including a discussion of fluorophores, is set forth in a chapter entitled "Fluorescent-labeled Immunoassay" in Edwards, Immunoassays: An Introduction, William Heinemann Medical Books, London, 1985, pp. 87–99.

The invention now being generally described, the same will be better understood by reference to the following detailed examples which are provided for purposes of illustration only and are not to be considered limiting of the invention unless so specified.

EXAMPLE

Solid Nylon Surfaces

The preparation of polyamide surfaces according to the present invention has been demonstrated using a dyeing technique designed for polyamide microporous membrane filter media from the Pall Corporation family of membrane filters. The dyeing technique was designed for such porous materials, particularly Pall Ultipor N66 (previously described).

Process Conditions for Preparation of Optically Passive Polyamides

A 2% (w/w) aqueous solution of an acid reactive dye is prepared. Two such dyes are Irgalan BGL200 TM from Ciba-Geigy, a premetalized sulfonic acid azodye, and Nylanthrene TM, a non-metallic acid-reactive dye from Crompton and Knowles. The dye solution is heated to and maintained in the range from 80° C. to 90° C. with stirring for 30 minutes. The thus-prepared dye bath is then cooled to about 45° C. Appropriate leveling agents were used in accordance with instructions provided by the dye manufacturer.

A dry membrane is then wetted by the dye solution by immersion of the membrane. The immersed membrane is kept in the dye solution at 85°–90° C. for at least 5 minutes.

Following the membrane soak, the bath is cooled to about 45° C. with the membrane still immersed. The membrane is then removed from the dye bath and washed with deionized water to remove unreacted dye. The washed, dyed membrane is dried for about 10 minutes at 100° C.

Properties of Dyed Membranes

The product membranes have a homogeneous black appearance and exhibit no evidence of fluorescence when irradiated by ultraviolet light at wavelengths of about 254 nm and 365 nm. Additionally, laboratory evaluation of the dyed membranes indicated that surface characteristics and porosity were not adversely affected.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In an assay in which the presence or quantity of an analyte is being detected by fluorescence at an emission waveband of light as a result of excitation of a fluorescent signal material at an excitation waveband of light and in which said excitation waveband of light impinges upon a polyamide, an improvement which comprises:

providing as said polyamide an optically passive polyamide prepared by dyeing a polyamide substrate with a reactive dye having an absorbance spectrum selected to overlap said excitation waveband or said emission waveband or both of said wavebands.

2. The assay of claim 1 wherein said dye absorbs substantially all wavelengths of visible and ultraviolet light greater than the minimum wavelength of said excitation waveband.

3. The assay of claim 1 wherein said dye is a premetallized reactive dye.

4. The assay of claim 1 wherein said polyamide is a container or a wall of a container in which said assay is being conducted.

5. The assay of claim 1 wherein said polyamide is a particle to which a reactant used in said assay is attached.

6. The assay of claim 1 wherein said polyamide is a porous nylon-6,6 chemically-modified membrane.

7. The assay of claim 1 wherein said optically passive polyamide is a microporous membrane.

8. The assay of claim 7 wherein said assay is a particle concentration fluorescence immunoassay.

9. The assay of claim 1 wherein in said dye is an acid reactive azo dye.

10. The assay of claim 9, wherein said dye is a non-metallic acid reactive azo dye of the formula Ar—N=N—Ar', wherein Ar and Ar' independently represent an aromatic ring system having substituents selected from the group consisting of hydrogen, $C_1$–$C_4$ alkyl, carboxyl, hydroxyl, amino, amino substituted with 1 or 2 $C_1$–$C_4$ alkyl groups, $C_1$–$C_4$ alkoxy, nitro, halo, sulfate, sulfonyl, sulfonamide, $C_1$–$C_4$ sulfate or sulfonyl ester, and substituted or unsubstituted aromatic groups.

* * * * *